US00PP08931P

United States Patent [19]

Marciel et al.

[11] Patent Number: Plant 8,931

[45] Date of Patent: Oct. 11, 1994

[54] HYBRID TEA ROSE PLANT NAMED DEVSPILIO

[75] Inventors: Stanley G. Marciel; Jeanne A. Marciel, both of Aptos, Calif.

[73] Assignee: DeVor Nurseries, Inc., Watsonville, Calif.

[21] Appl. No.: 148,826

[22] Filed: Nov. 4, 1993

[51] Int. Cl.[5] ..... A01H 5/00

[52] U.S. Cl. ..... Plt./14

[58] Field of Search ..... Plt. 14

*Primary Examiner*—Howard J. Locker

*Attorney, Agent, or Firm*—Christie, Parker & Hale

[57] ABSTRACT

A new hybrid tea rose plant producing white flowers.

1 Drawing Sheet

SUMMARY OF THE INVENTION

The present invention relates to a new and distinct variety of rose plant of the hybrid tea rose class which was originated by crossing as seed parent and pollen parent unnamed and unpatented seedlings of our creation. The varietal denomination of which new rose is 'Devspilio'.

Among the novel characteristics possessed by this new variety which distinguish it from its parents and all other varieties of which I am aware are its attractive well formed white flowers borne on a plant particularly suitable for use for cut-flower production in greenhouses. Flowers, which are borne on long stems, are clear white.

Asexual reproduction by budding of the new variety as performed in Watsonville, Calif. shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage Seedling.

*Seed parent.*—Unnamed seedling.

*Pollen parent.*—Unnamed seedling.

Class: Hybrid tea.

The following is a detailed description of my new variety, of new specimens grown under glass in Watsonville, Calif. in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Continuous.

A. Bud:

(1) *Size.*—Medium.

(2) *Form.*—Pointed, slender.

(3) *Color.*—Before sepals divide, near 146C.

(4) *Sepals.*—Upright and close to bud, then spreading and reflexing; some sepals are foliaceous. Color: Near 146A.

(5) *Peduncle.* Length: About 16–20 cm. Aspect: Straight. Strength: Erect, Sturdy. Color: Near 144A.

(6) *Bracts.*—From 1 to 2, close to ovate, 10–12 cm below calyx, near 147A.

B. Bloom:

(1) *Size.*—Average size when fully expanded — about 9–11 cm.

(2) *Borne.*—Singly, one to a stem (3) *Form.*—Imbricated, becoming flat, petals roll under slightly at maturity.

(4) *Petalage.*—Number of petals under normal conditions — about 26–30.

(5) *Color.*—⅓ to ½ open: top surface of outer petals is near 155D to C to near 155B toward petal base, with base near 3C; undersurface of outer petals is near 155D to near 155D toward base, with base near 150C; top surface of inner petals is near 155D with near 155B near base, with base near 5C; undersurface of inner petals is near 155D with near 155D near base, and 154C at base; color at point of petal attachment is near 154C and the general tonality from a distance is white. Fully open blooms: top surface of outer petals is near 155D to near 155A toward petal base, with base near 4D; undersurface of outer petals is near 155D to near 156D toward base, with base near 4D; top surface of inner petals is near 155D with near 157C near base, with base near 5D; undersurface of inner petals is near 155D with near 156D near base, and 5D at base; color at point of petal attachment is near 4D and the general tonality from a distance is white. Color of bloom upon aging deepens, with the petal top surface near 155D to 156C and the petal undersurface near 156D.

C. Petals:

(1) *Texture.*—Medium.

(2) *Appearance.*—Inside and outside are smooth with a matte finish.

(3) *Form.*—Smooth, ordinary.

(4) *Arrangement.*—Regularly arranged, imbricated.

(5) *Petaloids.*—Few.

(6) *Fragrance.*—None.

(7) *Lasting quality.*—7–10 days as cut flower; petals hold well for greenhouse variety.

REPRODUCTIVE ORGANS

A. Stamens:
(1) *Color.*—Near 167C.
(2) *Arrangement.*—Regularly arranged.
(3) *Anthers.*—Color near 167C.
(4) *Filaments.*—Color near 167D, middle orange white.
(5) *Pollen.*—Color near 19B.

B. Pistils:
(1) *Styles.*—Bunched, uneven length.
(2) *Stigmas.*—Color near 63A.

C. Characteristics of hips: Globose, about 3.5 cm by 3.5 cm; seeds slightly protrude; near 167A at maturity.

PLANT

A. Form: Upright.

B. Growth: Very vigorous, uniform branching; height attained about 254–292 cm at first season.

C. Foliage: Compound 3–5 leaflets.
(1) *Size.*—Large.
(2) *Quantity.*—Abundant.
(3) *Color.*—New foliage — upper side near 147A, underside near 191A; old foliage — upper side near 147A, underside near 191A.
(4) *Shape.*—Mucronate.
(5) *Texture.*—Leathery, smooth.
(6) *Edge.*—Serrate.
(7) *Serration.*—Denticulate.

(8) *Leaf stem.*—Color — medium green
(9) *Stipules.*—Medium length, hairy, almost parallel and reflexing.
(10) *Rachis.*—Small prickles.
(11) *Petioles.*—Top near 146A, underside near 146B.
(12) *Auricle.*—Slender and triangular.
(13) *Resistance to disease.*—Under greenhouse conditions no rust and blackspot; good resistance to mildew.

D. Wood:
(1) *New wood.*—Color purplish-green, bark smooth.
(2) *Old wood.*—Color near 146B to 146A, bark smooth.

E. Flower stem: About 75–85 cm from last cut.

F. Thorns:
(1) *Thorns.* Quality: On main stalk, ordinary; on laterals from stalk, very few. Form: Thin, straight, slightly wing-shaped. Length: Variable. Color: Near 146D when young. Position: Irregular.
(2) *Prickles.*—Profuse.

G. Winter hardiness: Greenhouse vareiety; wintered well in California.

I claim:

1. A new and distinct variety of rose plant of the hybrid tea rose class, substantially as shown and described.

* * * * *

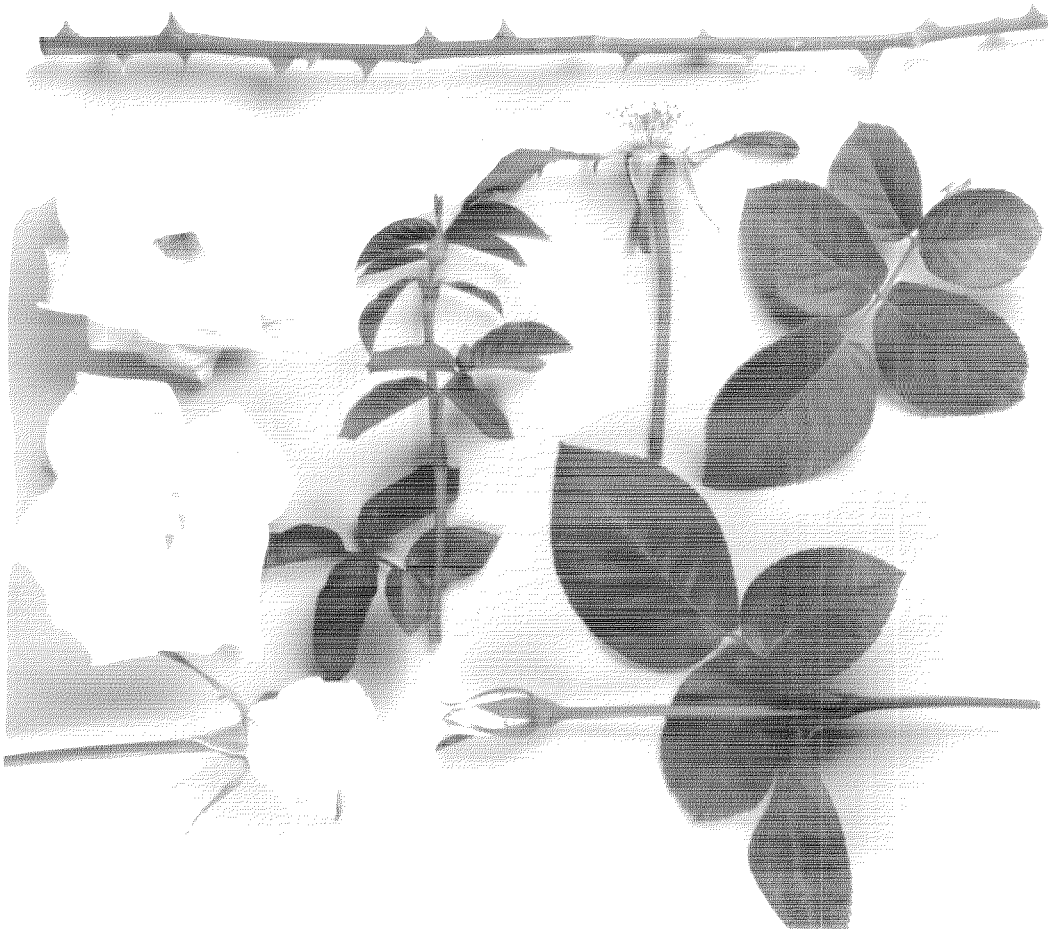

UNITED STATES PATENT AND TRADEMARK OFFICE

CERTIFICATE OF CORRECTION

PATENT NO. : Plant 8,931

DATED : October 11, 1994

INVENTOR(S) : Stanley G. Marciel; Jeanne A. Marciel

It is certified that error appears in the above-indentified patent and that said Letters Patent is hereby corrected as shown below:

On the Title Page, Item 56

After [58] insert the following reference:
-- [56] Reference Cited
U.S. PATENT DOCUMENT
P.P. 2,132 3/1961 Swim, et al...Plt.14 --.

Column 1, line 7 after "varietal" change "denomination of which" to --denomination of this--.
Column 4, line 17, change "Quality" to -- Quantity --.
Column 4, line 23, change "vareiety" to -- variety --.

Signed and Sealed this

Second Day of May, 1995

*Attest:*

Bruce Lehman

BRUCE LEHMAN

*Attesting Officer*

*Commissioner of Patents and Trademarks*